United States Patent
Irwin et al.

(10) Patent No.: US 8,911,501 B2
(45) Date of Patent: Dec. 16, 2014

(54) CRUCIATE-RETAINING TIBIAL PROSTHESIS

(75) Inventors: Ronald R. Irwin, Stuart, FL (US);
Jason Karl Otto, Plantation, FL (US);
Ali Zafar Abbasi, Davie, FL (US);
Mark Ellsworth Nadzadi, Memphis, TN (US)

(73) Assignee: Mako Surgical Corp., Fort Lauderdale, FL (US)

(*) Notice: Subject to any disclaimer, the term of this patent is extended or adjusted under 35 U.S.C. 154(b) by 0 days.

(21) Appl. No.: 13/340,645

(22) Filed: Dec. 29, 2011

(65) Prior Publication Data
US 2013/0173010 A1 Jul. 4, 2013

(51) Int. Cl.
*A61F 2/38* (2006.01)

(52) U.S. Cl.
CPC ............................ *A61F 2/38* (2013.01)
USPC ................................................ 623/20.32

(58) Field of Classification Search
CPC ........... A61F 2/389; A61F 2002/30324; A61F 2002/30327; A61F 2002/4205; A61F 2/3868; A61F 2002/30387; A61F 2002/30879; A61F 2002/3696
USPC ............................. 623/20.14–20.36
See application file for complete search history.

(56) References Cited

U.S. PATENT DOCUMENTS

| | | | |
|---|---|---|---|
| 3,798,679 A | 3/1974 | Ewald | |
| 3,816,855 A * | 6/1974 | Saleh | 623/20.31 |
| 3,869,731 A | 3/1975 | Waugh et al. | |
| 4,207,627 A * | 6/1980 | Cloutier | 623/20.21 |
| 4,586,933 A | 5/1986 | Shoji et al. | |
| 4,711,639 A | 12/1987 | Grundei | |
| 4,769,040 A | 9/1988 | Wevers | |
| 4,822,362 A | 4/1989 | Walker et al. | |
| 5,037,439 A | 8/1991 | Albrektsson et al. | |

(Continued)

FOREIGN PATENT DOCUMENTS

| | | |
|---|---|---|
| EP | 0306744 A2 | 3/1989 |
| EP | 1011542 A1 | 6/2000 |

(Continued)

OTHER PUBLICATIONS

International Search Report and Written Opinion for International Application No. PCT/US2012/070531, mailed May 27, 2013, 18 pages.

(Continued)

*Primary Examiner* — David Isabella
*Assistant Examiner* — Ann Schillinger
(74) *Attorney, Agent, or Firm* — Lerner, David, Littenberg, Krumholz & Mentlik, LLP

(57) ABSTRACT

A tibial prosthesis comprises a medial base portion configured to engage a medial surface of a tibia and a lateral base portion configured to engage a lateral surface of the tibia. At least a portion of the medial and lateral base portions are separated by a passage interposed therebetween. The tibial prosthesis also comprises a bridge coupling the medial base portion and the lateral base portion, wherein at least a portion of the bridge is elevated above a portion of the passage between the medial base portion and the lateral base portion. The bridge may define an underlying area that receives at least a portion of a tibial eminence when the tibial prosthesis is engaged with the tibia, wherein the height of the bridge varies in a superior direction across the passage.

25 Claims, 15 Drawing Sheets

(56) References Cited

U.S. PATENT DOCUMENTS

| | | | |
|---|---|---|---|
| 5,137,536 A | 8/1992 | Koshino | |
| 5,171,283 A | 12/1992 | Pappas et al. | |
| 5,282,868 A | 2/1994 | Bahler | |
| 5,509,934 A | 4/1996 | Cohen | |
| 5,658,341 A | 8/1997 | Delfosse | |
| 5,702,464 A | 12/1997 | Lackey et al. | |
| 5,755,801 A | 5/1998 | Walker et al. | |
| 5,824,103 A | 10/1998 | Williams | |
| 5,879,394 A | 3/1999 | Ashby et al. | |
| 6,258,127 B1 | 7/2001 | Schmotzer | |
| 6,387,131 B1 | 5/2002 | Miehlke et al. | |
| 6,436,145 B1 | 8/2002 | Miller | |
| 6,482,209 B1 | 11/2002 | Engh et al. | |
| 6,558,421 B1 | 5/2003 | Fell et al. | |
| 6,652,588 B2 | 11/2003 | Hayes, Jr. et al. | |
| 6,679,914 B1 | 1/2004 | Gabbay | |
| 6,699,291 B1 | 3/2004 | Augoyard et al. | |
| 6,896,702 B2 | 5/2005 | Collazo | |
| 6,969,393 B2 | 11/2005 | Pinczewski et al. | |
| 7,060,101 B2 | 6/2006 | O'Connor et al. | |
| 7,066,963 B2 | 6/2006 | Naegerl | |
| 7,115,131 B2 | 10/2006 | Engh et al. | |
| 7,261,740 B2 | 8/2007 | Tuttle et al. | |
| 7,294,149 B2 | 11/2007 | Hozack et al. | |
| 7,458,933 B2 | 12/2008 | LeVahn et al. | |
| 7,462,199 B2 | 12/2008 | Justin et al. | |
| 7,578,850 B2 | 8/2009 | Kuczynski et al. | |
| 7,625,407 B2 | 12/2009 | Akizuki et al. | |
| 7,635,390 B1 | 12/2009 | Bonutti | |
| 7,695,519 B2 | 4/2010 | Collazo | |
| 7,758,652 B2 | 7/2010 | Engh et al. | |
| 7,766,969 B2 | 8/2010 | Justin et al. | |
| 7,771,483 B2 | 8/2010 | Justin et al. | |
| 7,771,484 B2 | 8/2010 | Campbell | |
| 7,799,086 B2 | 9/2010 | Justin et al. | |
| 7,828,852 B2 | 11/2010 | Bonutti | |
| 8,066,776 B2 | 11/2011 | O'Connor et al. | |
| 8,092,546 B2 | 1/2012 | Coon et al. | |
| 8,105,387 B2 | 1/2012 | Barnett et al. | |
| 8,114,165 B2 | 2/2012 | Rhodes et al. | |
| 8,128,703 B2 | 3/2012 | Hazebrouck et al. | |
| 8,137,407 B2 | 3/2012 | Todd et al. | |
| 8,157,869 B2 | 4/2012 | Metzger et al. | |
| 8,211,181 B2 | 7/2012 | Walker | |
| 8,292,964 B2 | 10/2012 | Walker | |
| 8,292,965 B2 * | 10/2012 | Walker | 623/20.27 |
| 8,343,227 B2 | 1/2013 | Metzger et al. | |
| 8,403,994 B2 | 3/2013 | Maloney et al. | |
| 8,500,818 B2 | 8/2013 | Metzger et al. | |
| 8,529,631 B2 * | 9/2013 | Donno et al. | 623/20.15 |
| 8,568,486 B2 | 10/2013 | Wentorf et al. | |
| 8,574,304 B2 | 11/2013 | Wentorf et al. | |
| 8,603,101 B2 | 12/2013 | Claypool et al. | |
| 8,613,775 B2 | 12/2013 | Wentorf et al. | |
| 2004/0030397 A1 | 2/2004 | Collazo | |
| 2004/0138755 A1 | 7/2004 | O'Connor et al. | |
| 2005/0283251 A1 | 12/2005 | Coon et al. | |
| 2006/0004460 A1 | 1/2006 | Engh et al. | |
| 2006/0195196 A1 | 8/2006 | Pendleton et al. | |
| 2006/0212124 A1 | 9/2006 | Siebel | |
| 2006/0265079 A1 | 11/2006 | D'Alessio | |
| 2007/0010890 A1 | 1/2007 | Collazo | |
| 2007/0203582 A1 | 8/2007 | Campbell | |
| 2008/0119941 A1 | 5/2008 | Seo et al. | |
| 2009/0187251 A1 | 7/2009 | Justin et al. | |
| 2009/0270995 A1 | 10/2009 | Rhodes et al. | |
| 2009/0319048 A1 | 12/2009 | Shah et al. | |
| 2010/0016980 A1 | 1/2010 | Donno et al. | |
| 2010/0280624 A1 | 11/2010 | Engh et al. | |
| 2010/0305575 A1 | 12/2010 | Wilkinson et al. | |
| 2010/0305710 A1 | 12/2010 | Metzger et al. | |
| 2010/0305711 A1 | 12/2010 | McKinnon et al. | |
| 2010/0331847 A1 | 12/2010 | Wilkinson et al. | |
| 2010/0331848 A1 | 12/2010 | Smith et al. | |
| 2010/0331991 A1 | 12/2010 | Wilkinson et al. | |
| 2011/0015749 A1 | 1/2011 | Engh et al. | |
| 2011/0066248 A1 | 3/2011 | Ries et al. | |
| 2011/0066249 A1 | 3/2011 | Justin et al. | |
| 2011/0082559 A1 | 4/2011 | Hartdegen et al. | |
| 2011/0098824 A1 | 4/2011 | Jukes et al. | |
| 2011/0190898 A1 | 8/2011 | Lenz et al. | |
| 2011/0264097 A1 | 10/2011 | Hodorek et al. | |
| 2012/0035736 A1 | 2/2012 | O'Connor et al. | |
| 2012/0078262 A1 | 3/2012 | Pinczewski et al. | |
| 2012/0179266 A1 | 7/2012 | Collazo | |
| 2012/0209394 A1 | 8/2012 | Bojarski et al. | |
| 2012/0316563 A1 | 12/2012 | Metzger et al. | |
| 2012/0330429 A1 | 12/2012 | Axelson, Jr. et al. | |
| 2013/0006375 A1 | 1/2013 | Metzger et al. | |
| 2013/0024001 A1 | 1/2013 | Wentorf et al. | |
| 2013/0046385 A1 | 2/2013 | Hartdegen et al. | |
| 2013/0131817 A1 | 5/2013 | Parisi et al. | |
| 2013/0131819 A1 | 5/2013 | Parisi et al. | |
| 2013/0173010 A1 | 7/2013 | Irwin et al. | |
| 2013/0204383 A1 | 8/2013 | Wentorf | |
| 2013/0245777 A1 | 9/2013 | Jerry | |
| 2013/0289731 A1 | 10/2013 | Katerberg et al. | |
| 2013/0345820 A1 | 12/2013 | Maloney et al. | |
| 2014/0025175 A1 | 1/2014 | Wentorf et al. | |
| 2014/0025176 A1 | 1/2014 | Wentorf et al. | |
| 2014/0025177 A1 | 1/2014 | Wentorf et al. | |
| 2014/0067076 A1 | 3/2014 | Collazo | |

FOREIGN PATENT DOCUMENTS

| | | |
|---|---|---|
| FR | 2676916 | 12/1992 |
| WO | 9858603 A1 | 12/1998 |
| WO | 0076428 A1 | 12/2000 |
| WO | 2006012370 A2 | 2/2006 |
| WO | 2009158318 A1 | 12/2009 |
| WO | 2010006677 A1 | 1/2010 |
| WO | 2010138836 A2 | 12/2010 |
| WO | 2010138841 A2 | 12/2010 |
| WO | 2010138850 A2 | 12/2010 |
| WO | 2010138854 A2 | 12/2010 |
| WO | 2010138857 A2 | 12/2010 |
| WO | 2011094540 A2 | 8/2011 |
| WO | 2012178031 | 12/2012 |
| WO | 2013101582 | 7/2013 |
| WO | 2013148954 | 10/2013 |

OTHER PUBLICATIONS

Invitation to Pay Additional Fees and Communication Relating to the Results of the Partial International Search for International Application No. PCT/US2012/070531, mailed Mar. 6, 2013, 7 pages.
Pritchett, James W., BioPro: Equalizer Modular Total Knee Replacement, available at least as early as 1999, 19 pages.
Townley, Charles O., Total Knee Arthroplasty: A Personal Retrospective and Prospective Review, Clinical Orthopaedics and Related Research, No. 236, 1988, 15 pages.
BioPro, Equalizer Modular Total Knee Replacement, date not known.
Freeman-Swanson Total Knee Prosthesis, Vitallium Alloy Femoarl Component, 1978.
Howmedica, Inc. Cruciate-Condylar Total Knee Surgical Technique, 1979.
Howmedica, Inc. The Howmedica Kinematic Knee System, 1980.
International Search Report and Written Opinion for Application No. PCT/US2014/017664 dated Jun. 6, 2014.
International Search Report and Written Opinion, PCT/US2012/0020719, dated Mar. 19, 2012.
Partial International Search Report for Application No. PCT/US2014/017664 dated Apr. 16, 2014.
Townley Total Knee Prosthesis, Vitallium Alloy Femoral Component, 1978.
Townley, Charles 0., Total Knee Arthroplasty: A Personal Retrospective and Prospective Review, Clinical Orthopaedics and Related Research, No. 236, 1988, 15 pages.

\* cited by examiner

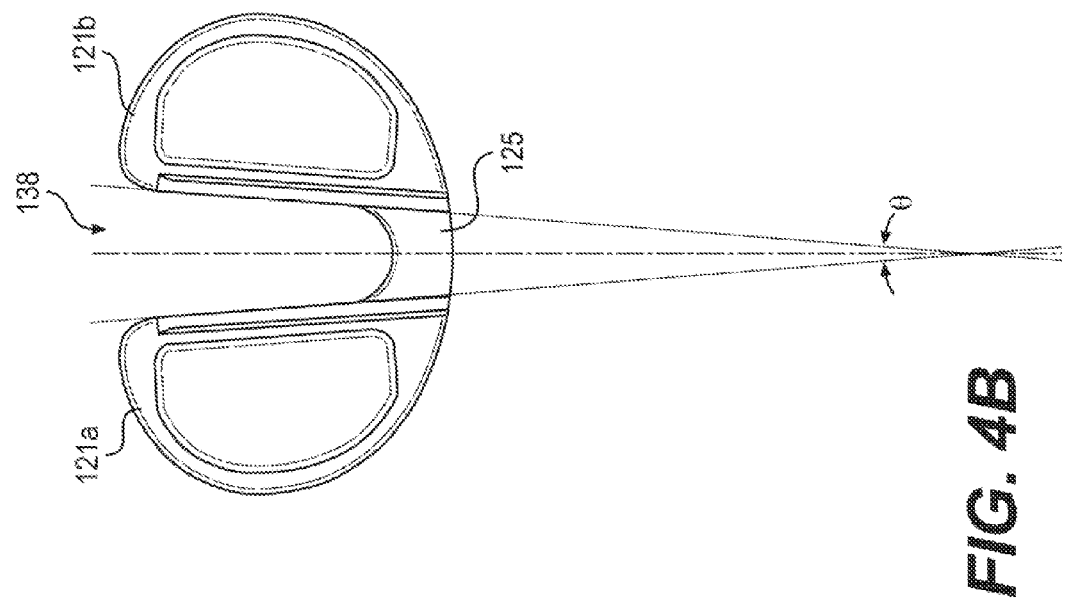
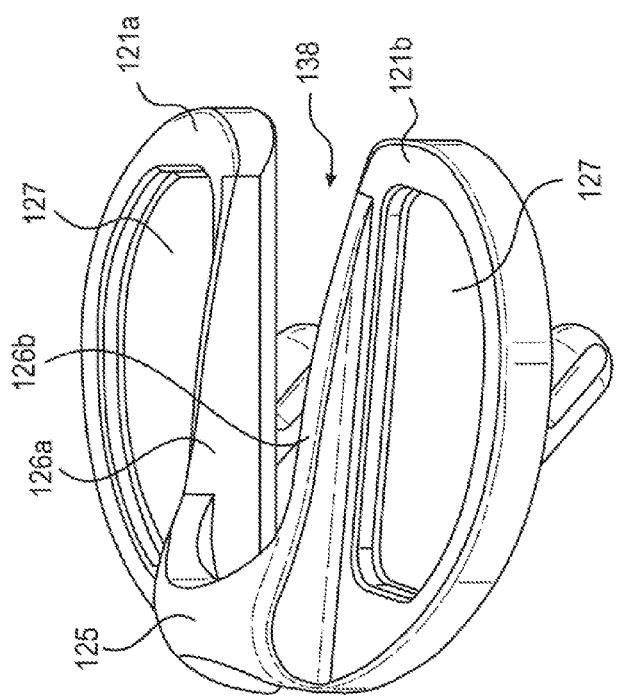
FIG. 4A
FIG. 4B

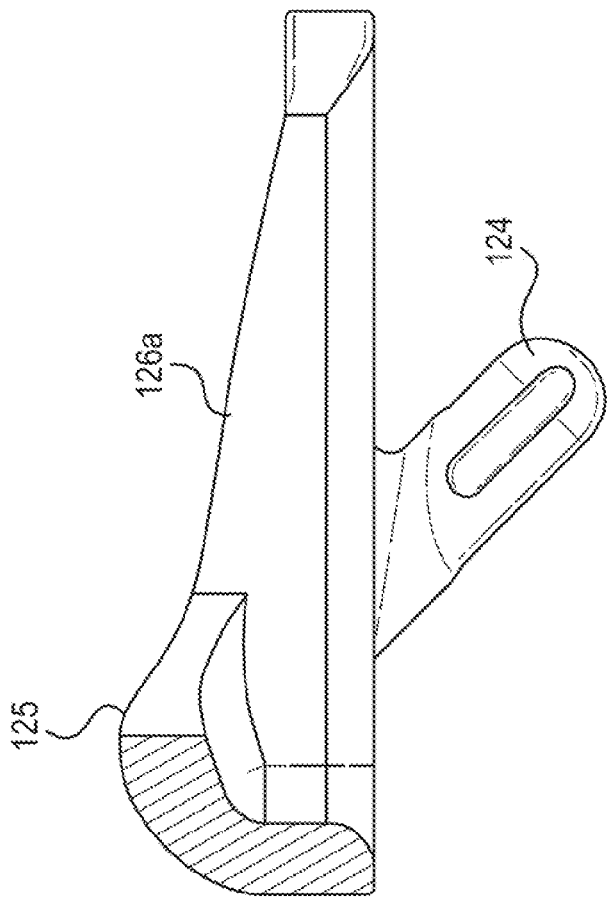
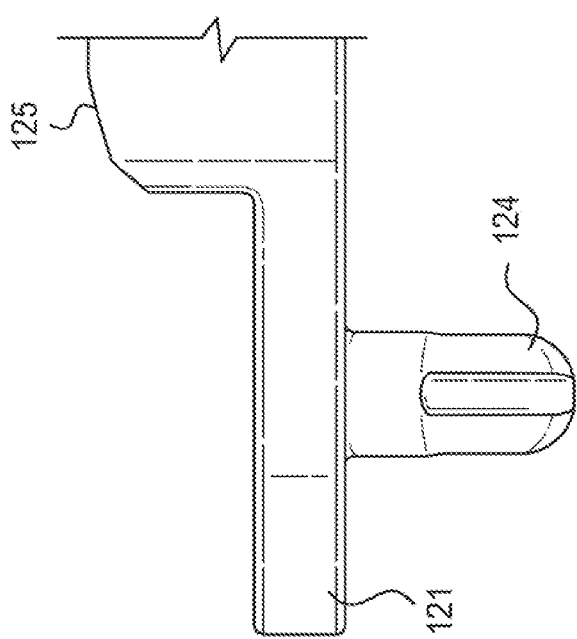
FIG. 6B
FIG. 6A

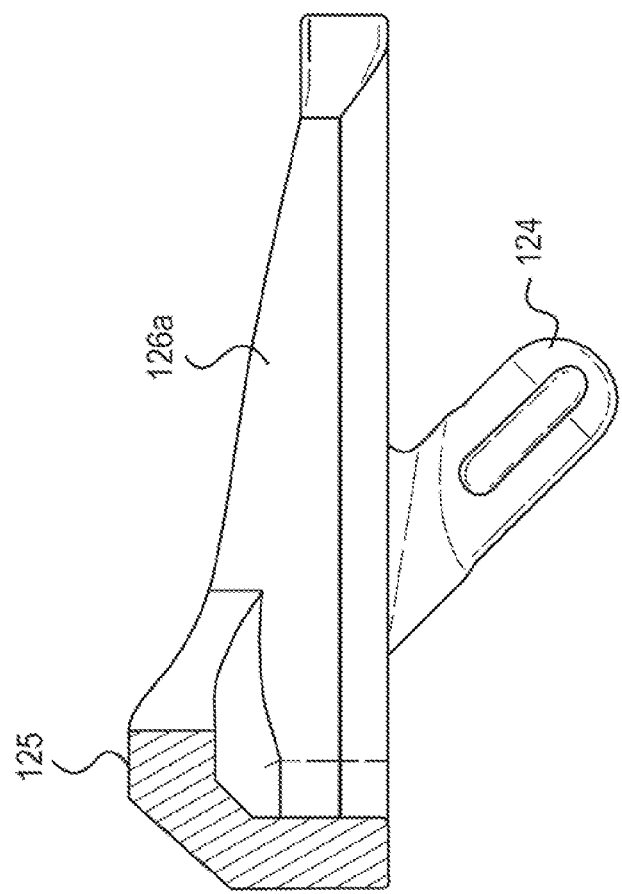
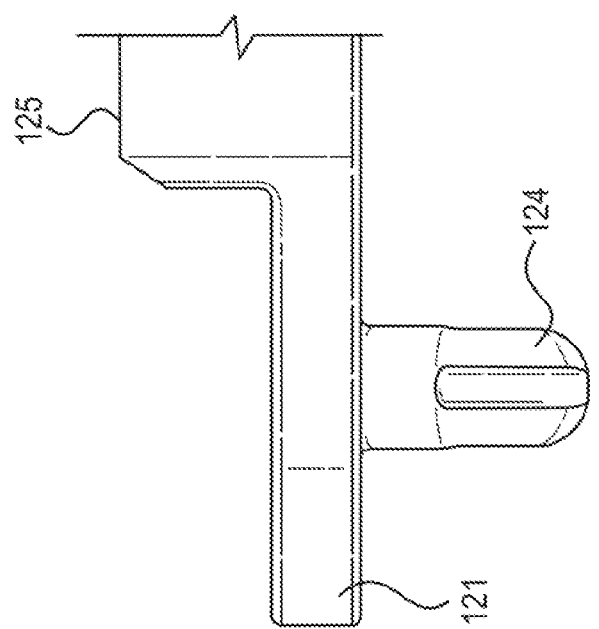
FIG. 7B
FIG. 7A

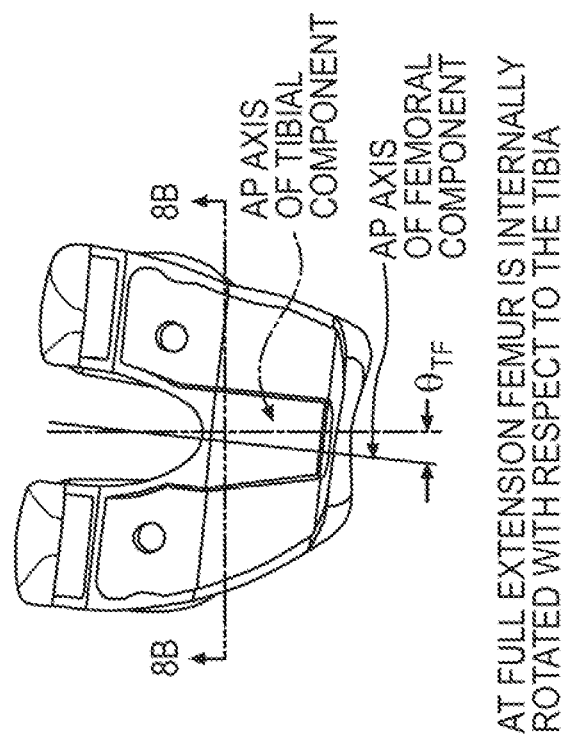
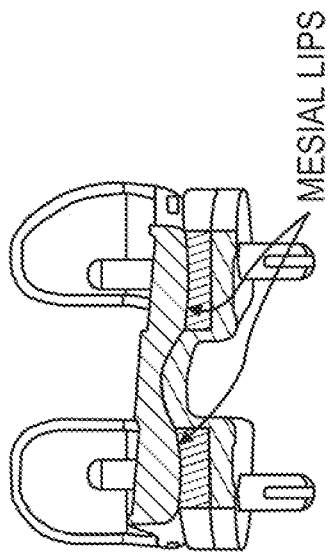

MEDIAL EXTENDS MORE POSTERIOR THAN LATERAL $AP_M > AP_L$

SUBSTANTIALLY ARCUATE

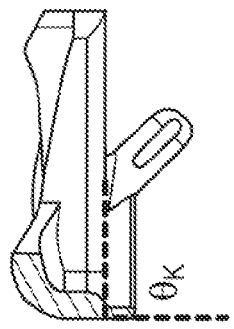
FIG. 14B
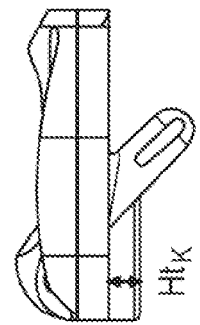
FIG. 15C
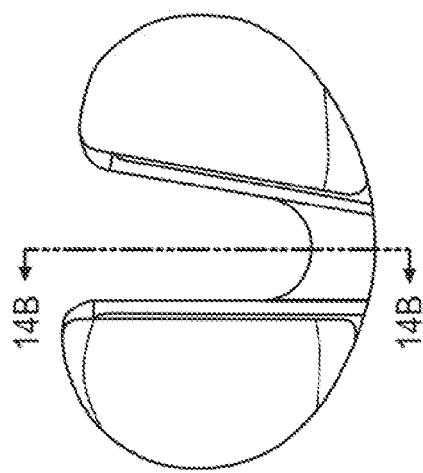
FIG. 14A
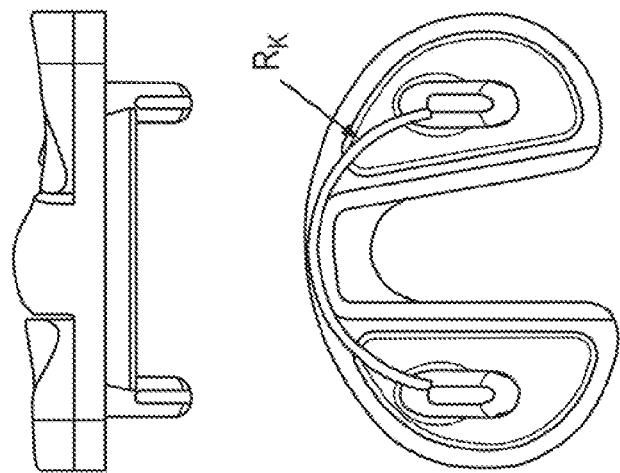
FIG. 15A
FIG. 15B

BENDED EDGES

KEEL RADIUS SUBSTANTIALLY MATCHES PERIMETER PROFILE

CRUCIATE-RETAINING TIBIAL PROSTHESIS

TECHNICAL FIELD

The present disclosure relates generally to orthopedic prosthesis systems used in knee joint replacement surgeries and, more particularly, to a tibial prosthesis used in cruciate-retaining knee arthroplasty procedures.

BACKGROUND

The knee joint comprises the interface between the distal end of the femur and the proximal end of the tibia. In a properly-functioning knee joint, medial and lateral condyles of the femur pivot smoothly along menisci attached to respective medial and lateral condyles of the tibia. When the knee joint is damaged, the natural bones and cartilage that form the joint may be unable to properly articulate, which can lead to joint pain and, in some cases, interfere with normal use of the joint.

In some situations, surgery is required to restore normal use of the joint and reduce pain. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replicate the resected tissue and restore proper knee joint operation.

One knee replacement procedure—total knee arthroplasty ("TKA")—involves the resection of some or all of each of the medial and lateral condyles of both the femur and tibia and the removal of the fibro-cartilage menisci located at the femorotibial interface. A prosthetic femoral component, typically made of cobalt-chromium alloy or other strong, surgical-grade metal, is fitted and secured to the distal end of the femur to replace the resected portion of the femur. Similarly, a prosthetic tibial component, the base of which is also typically made of cobalt-chromium alloy, titanium, or other suitable metal, is fitted and secured to the proximal end of the tibia to replace the resected portion of the tibia.

In some situations, the patient's bone at the knee joint may have deteriorated to a point which requires TKA surgery, but one or more of the patient's cruciate ligaments (e.g., the anterior cruciate ligament (ACL) and/or posterior cruciate ligament (PCL)) are in sufficient condition to provide adequate joint stability. Maintaining the native cruciate ligaments is often advantageous, as doing so is generally thought to aid in proprioception (the ability to sense where parts of the body are in relation to each other) and could make activities like climbing stairs feel more stable or natural. Preserving the cruciate ligaments can also promote more normal front to back knee motion, which can enhance the patient's ability to maintain pre-operative range of motion, particularly as it relates to deep flexion. The ligaments also aid in joint stability.

Each of the native cruciate ligaments connects to one of the femoral condyles, passes within the intercondylar region of the femur, and connects to the center-top portion of the tibia called the tibial eminence. In order to accommodate the passage of the cruciate ligaments, the femoral and tibial implant components used in cruciate-retaining procedures typically comprise intercondylar cutaways that define a vertical passage between the intercondylar fossa of the femur and the tibial eminence. The medial and lateral components of each of the femoral and tibial prosthetic components are separated by a deep intercondylar passage (or "notch") that allows for passage of cruciate ligaments vertically through the notch.

During normal operation of the knee joint, the cruciate ligaments can exert significant tension at the attachment site of the tibia called the tibial eminence. In a healthy knee joint, there is sufficient tissue surrounding the tibial eminence to aid in the distribution of this force across the surface of the tibia. Installation of a cruciate-retaining tibial prosthetic component, while aimed at preserving an attachment site at the tibial eminence, typically requires significant removal of the surrounding native tissue of the tibia to make way for installation of the tibial implant. Unfortunately, this surrounding tissue provides much of the attachment strength that counteracts the tension applied by the cruciate ligaments. Consequently, removal of this tissue can substantially weaken the attachment strength of the tibial eminence. One major problem associated with cruciate-retaining tibial procedures is the incidence of failure of the tibial eminence due to the removal of surrounding supporting structure that is required by the installation of the tibial prosthetic.

Early solutions for addressing the problem of tibial eminence failure were aimed at increasing the width of the intercondylar notch of the tibial prosthetic, which, in turn, increased the amount of native bone that could be preserved in the area immediately surrounding the tibial eminence. Although the increased width of the intercondylar notch increased the attachment strength of the tibial eminence, it had several drawbacks. For example, increasing the width of the intercondylar notch resulted in a corresponding increase in the width of the structure used to connect the medial base portion to the lateral base portion. This increase in width resulted in a corresponding decrease in the structural integrity of the connecting structure. Thus, while a wider intercondylar notch tended to increase the attachment strength of the tibial eminence, it led to a significant reduction in the strength of the tibial prosthetic component.

In order to increase the structural integrity of the implant, some prosthetic designs utilize a support system that comprises a network of interconnected keels provided on the underside of the implant. This support system is designed for insertion into corresponding voids in the bone that are created by the surgeon during the knee replacement procedure. Although these systems may enhance the overall strength of the implant and allow for a wider intercondylar passage, they require removal of a significant amount of subsurface tissue, which can undermine the area surrounding the tibial eminence. This may compromise the strength of the area beneath the tibial eminence, which may result in increased incidence of failure of the tibial eminence.

The presently disclosed tibial prosthetics for cruciate-retaining knee arthroplasty procedures are directed to overcoming one or more of the problems set forth above and/or other problems in the art.

SUMMARY

In accordance with one aspect, the present disclosure is directed to a tibial prosthesis comprising a medial base portion configured to engage a medial surface of a tibia and a lateral base portion configured to engage a lateral surface of the tibia. At least a portion of the medial and lateral base portions are separated by a passage interposed therebetween. The tibial prosthesis also comprises a bridge coupling the medial base portion and the lateral base portion, wherein at least a portion of the bridge is elevated above a portion of the passage between the medial base portion and the lateral base portion. The bridge may define an underlying area that receives at least a portion of a tibial eminence when the tibial prosthesis is engaged with the tibia. The height of the bridge may vary in a superior direction across the passage.

According to another aspect, the present disclosure is directed to a tibial prosthesis comprising a medial base portion configured to engage a medial surface of a tibia and a lateral base portion configured to engage a lateral surface of the tibia. At least a portion of the medial and lateral base portions are separated by a passage interposed therebetween. The tibial prosthesis may also comprise a bridge coupling the medial base portion and the lateral base portion, wherein at least a portion of the bridge is elevated above a portion of the passage between the medial base portion and the lateral base portion. The bridge may define an underlying area that receives at least a portion of a tibial eminence when the tibial prosthesis is engaged with the tibia, wherein the bridge is asymmetric about a sagittal plane associated with the tibial prosthesis.

In accordance with yet another aspect, the present disclosure is directed to a tibial prosthesis comprising a medial base portion configured to engage a medial surface of a tibia and comprising a lip formed along a mesial edge of the medial base portion and a lateral base portion configured to engage a lateral surface of the tibia and comprising a lip formed along a mesial edge of the lateral base portion. The tibial prosthesis may also comprise a medial insert portion configured to engage a recess formed in the medial base portion and a lateral insert portion configured to engage a recess formed in the lateral base portion. The medial and lateral insert portions may each comprise a flange formed along a mesial edge of the respective insert portion and configured to protect at least a portion of the lip from contact by a femoral component. The tibial prosthesis may also comprise an arched bridge coupling the medial base portion and the lateral base portion, wherein at least a portion of the arched bridge is elevated above a portion of the passage between the medial base portion and the lateral base portion. The arched bridge may define an underlying area that accommodates at least a portion of a tibial eminence when the tibial prosthesis is engaged with the tibia. The width of the passage between the medial base portion and the lateral base portion may increase from the anterior of the tibial prosthesis to the posterior of the tibial prosthesis.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments that, together with the description, serve to explain the principles and features of the present disclosure.

FIG. 4A provides a perspective side view of an exemplary cruciate-retaining tibial prosthesis having an arched bridge, consistent with the disclosed embodiments;

FIG. 4B provides a top view of an exemplary cruciate-retaining tibial prosthesis, consistent with the disclosed embodiments;

FIGS. 6A and 6B provide a front hemispheric and side cross-sectional view, respectively, of an exemplary cruciate-retaining prosthetic system having an arched bridge, consistent with the disclosed embodiments;

FIGS. 7A and 7B provide a front hemispheric and side cross-sectional view, respectively, of an exemplary cruciate-retaining prosthetic system having an angled bridge, consistent with the disclosed embodiments;

FIGS. 8A and 8B provide a top view and front cross-sectional view, respectively, of an exemplary cruciate-retaining prosthetic system having an arcuate bridge, consistent with the disclosed embodiments;

FIGS. 14A and 14B provide a top view and side cross-sectional view, respectively, of an exemplary tibial component having an arcuate bridge and vertical, arcuate underside keel, consistent with the disclosed embodiments;

FIGS. 15A-15C provide a front view, bottom view, and side cross-sectional view, respectively, of an exemplary tibial component having an arcuate bridge and a vertical, arcuate underside keel, consistent with the disclosed embodiments;

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

A healthy knee joint comprises the interface between the distal end of the femur and the proximal end of the tibia. If the healthy knee joint becomes damaged due, for example, to injury or disease, knee surgery may be required to restore normal structure and function of the joint. If the damage to the knee is severe, total knee arthroplasty ("TKA") may be required. TKA typically involves the removal of the damaged portion of joint and the replacement of the damaged portion of the joint with one or more prosthetic components.

In some TKA procedures, one or more of cruciate ligaments (including anterior cruciate ligament and/or posterior cruciate ligament) may be left intact, to be re-used with the prosthetic implants to form the new knee joint. In these "cruciate-retaining" applications, the prosthetic implant components may be configured to avoid interference with or impingement on the retained cruciate ligaments passing through the intercondylar area of the knee joint. For example, each of the femoral and tibial prosthetic components may be designed with an intercondylar "notch" that extends from the posterior of the prosthetic component toward the anterior of the prosthetic component. The femoral and tibial intercondylar notches overlap in the vertical direction, providing a passage that allows the cruciate ligament to pass from the femoral intercondylar fossa down to the tibial eminence.

Figure 1:
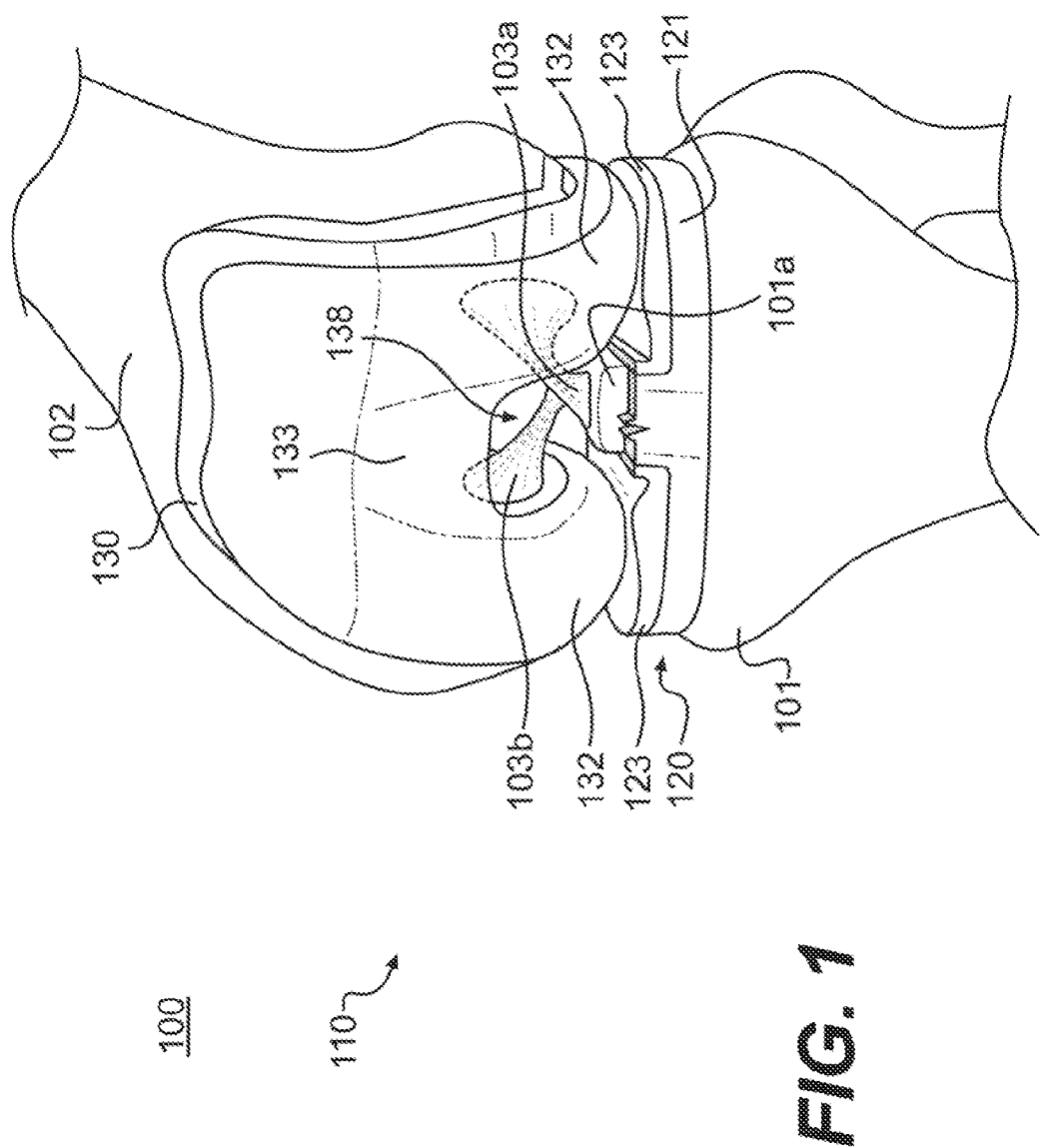
FIG. 1 illustrates a perspective view of post-operative prosthetic knee joint fitted with a cruciate-retaining prosthetic system, consistent with certain disclosed embodiments.

Because cruciate ligaments are exposed to significant tensile force during normal knee joint use, it is important that the attachment sites where the cruciate ligaments attach to the femur and tibia have sufficient strength to properly anchor the cruciate ligaments to the bone. Otherwise, the force applied by the cruciate ligament strains the tissue around the attachment site, possibly leading to failure of the joint, which may require corrective surgery to repair. One way to limit the possibility of such a failure is to limit the amount of bone resected at or near the attachment site(s) (i.e., the intercondylar fossa of the femur and tibial eminence 101a of the tibia). Limiting the amount of disturbance of native tissue at the attachment sites helps preserve the natural anchoring mechanism of the tissue, which decreases the likelihood of failure at the attachment site. As will be explained in greater detail below, prosthetic systems consistent with the presently disclosed embodiments may limit the amount of bone resection that is required for a TKA procedure. FIG. 1 illustrates a perspective view of a knee joint 100 fitted with a prosthetic implant system 110 having a tibial implant system 120 that is configured to limit the amount of bone resection that is required at the surface of tibia 101.

In the embodiment illustrated in FIG. 1, prosthetic implant system 110 may comprise a plurality of components, each of which is configured to replace a resected portion of a native knee joint. According to one embodiment, prosthetic implant system 110 may include a tibial implant system 120 configured to replace a resected portion of a native tibia 101. Prosthetic implant system 110 may also include a femoral component 130 configured to replace a resected portion of a native femur 102. After implantation during knee replacement surgery, tibial implant system 120 and femoral component 130 cooperate to replicate the form and function of the native knee joint.

Femoral component 130 may be secured to the distal end of femur 102 and configured to replace the structure and function of the native femoral portion of knee joint 100. As such, femoral component 130 may be manufactured from surgical-grade metal or metal alloy material (such as surgical-grade steel, titanium or titanium alloy, a cobalt-chromium alloy, a zirconium alloy, or tantalum) that is substantially rigid for providing sufficient strength to support the forces required of the knee joint. According to one embodiment, femoral component 130 may embody a single component having a plurality of different structural features, each configured to perform a particular function associated with the knee joint 100. For example, femoral component 130 may comprise a pair of condyles 132, each of which is coupled to a patellar guide portion 133. The pair of condyles 132 may be separated from one another by an intercondylar notch 138, which provides a channel through which one or more cruciate ligaments 103, such as anterior cruciate ligament (ACL) 103a and/or posterior cruciate ligament (PCL) 103b, may pass.

Tibial implant system 120 may include a plurality of components that cooperate to provide a stable surface that articulates with femoral component 130 to restore proper knee joint function. As illustrated in FIG. 1, tibial implant system 120 may include a base portion 121 and one or more insert portions 123. During a knee replacement procedure, base portion 121 may be secured to the proximal end of the tibia 101, which has been surgically prepared by removing damaged bone and tissue and reshaping the healthy bone to receive the base portion 121. Once base portion 121 is secured to tibia 101, the surgeon completes assembly of tibial implant system 120 by engaging and securing insert portions 123 within base portion 121. Base portion 121 of tibial prosthetic system may be configured with a passage through the center to allow for connection between the retained cruciate ligaments 103 and tibial eminence 101a.

Base portion 121 may be configured to emulate the structure and function of the top surface of tibia 101. Thus, similar to femoral component 130, base portion 121 may be manufactured from surgical-grade metal or metal alloy material (such as surgical-grade steel, titanium or titanium alloy, a cobalt-chromium alloy, a zirconium alloy, or tantalum) that is substantially rigid for providing a stable base upon which to reconstruct the remainder of the prosthetic joint.

Insert portions 123 may be designed to emulate the form and function of certain components of the natural femorotibial interface, including, among other things, medial and lateral menisci of the knee joint. As such, insert portions 123 may be constructed of smooth, semi-rigid synthetic or semi-synthetic plastic, rubber, or polymer material. Insert portions 123 may be configured to provide a smooth surface that is designed to articulate with a femoral component 130 during normal knee operation. According to one embodiment, insert portions 123 are configured to removably engage with base portion 121. Accordingly, insert portions 123 are configured for periodic replacement if insert portions 123 deteriorate over time due, for example, to excessive wear.

Figure 2:
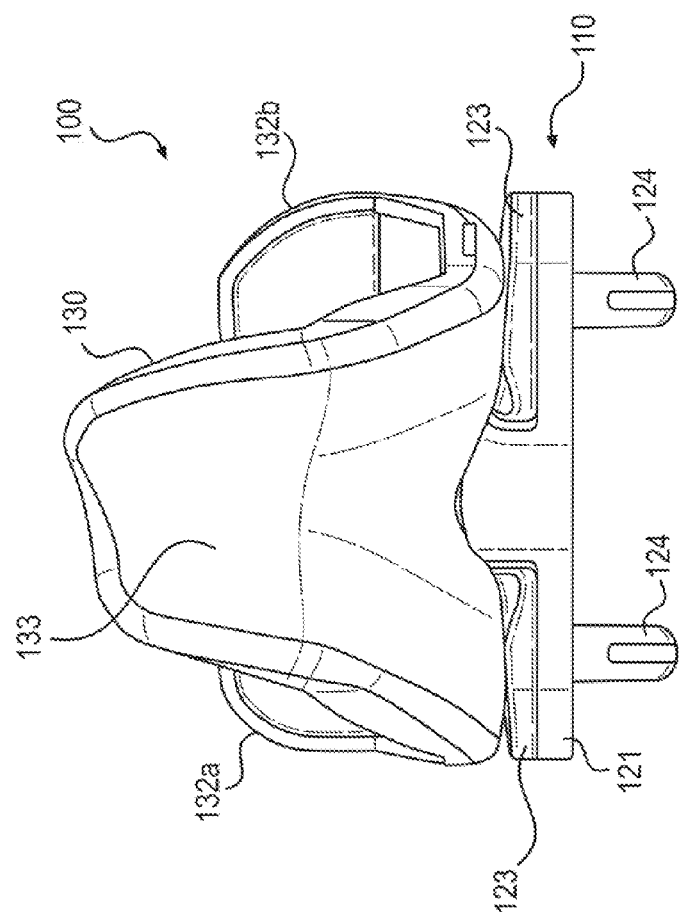
FIG. 2 illustrates a front view of a cruciate-retaining prosthetic system, in accordance with an exemplary embodiment.

FIG. 2 provides a front view of an exemplary prosthetic implant system 110. As noted above, prosthetic implant system 110 includes femoral component 130 that is configured to engage and articulate with insert portions 123 of base portion 121. During use, the femur 102 is rotated relative to tibia 101 during flexion and extension, causing femoral component 130 to rotate relative to base portion 121 across the top surface of insert portions 123.

As explained above, femoral component 130 comprises a patellar guide portion 133 and a pair of condyles 132, including a medial condyle 132a and a lateral condyle 132b. Patellar guide portion 133 of femoral component 130 may extend from the front of the distal end of the femur and curve downward toward the intercondylar fossa of the femur, which is exposed by intercondylar notch 138. Medial and lateral condyles 132a, 132h project from the bottom of patellar guide portion 133 and extend on either side of intercondylar notch 138 around the underside of the femur and continuing toward the posterior of the femur.

As noted above, tibial implant system 120 may comprise base portion 121 and insert portions 123, which cooperate to provide a stable surface that articulates with femoral component 130 to restore normal functionality of knee joint 100. To facilitate secure and stable engagement with the proximal end of tibia 101, base portion 121 of tibial implant system 120 may comprise one or more elongated projections 124 that protrude from a bottom surface of base portion 121. Elongated projections 124 may be inserted into corresponding holes that have been surgically formed within tibia 101 during a TKA procedure. Elongated projections 124 may be secured within the holes and configured to limit movement between tibial implant system 120 and tibia 101.

Figure 3:
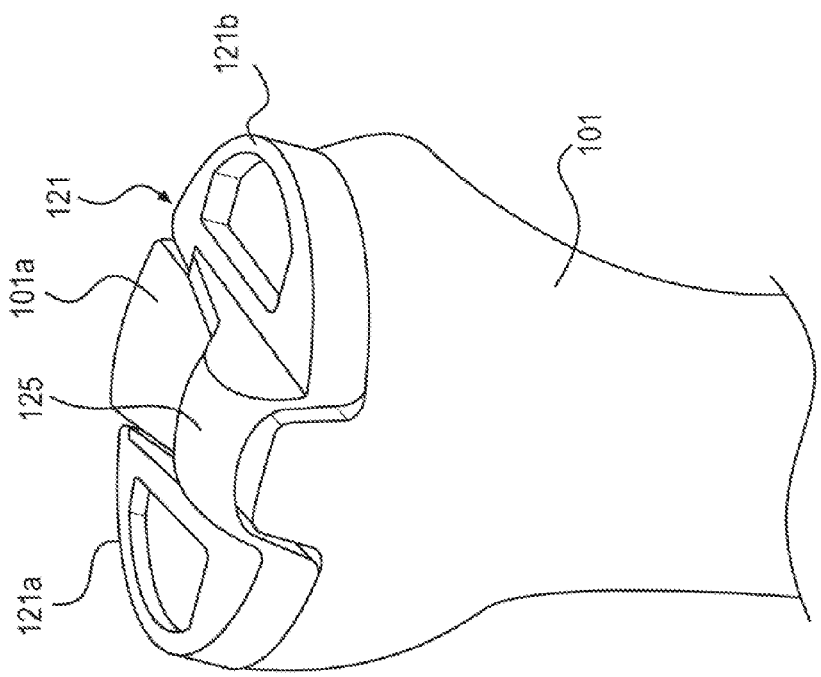
FIG. 3 illustrates a perspective view of a cruciate-retaining tibial prosthesis installed on a tibia, consistent with certain disclosed embodiments.

Tibial implant system 120 may be configured to limit the amount of bone resection that is required of tibia 101 without compromising the strength and stability of tibial base portion 121. By limiting the amount of bone resection, particularly in the area surrounding tibial eminence 101a, tibial implant system 120 may reduce the risk of premature failure of tibial eminence 101a. FIG. 3 illustrates an exemplary base portion 121 of tibial implant system 120 implanted on tibia 101.

As show in FIG. 3, base portion 121 may include a medial base portion 121a and a lateral base portion 121b, separated by an intercondylar passage interposed therebetween. Medial and lateral base portions 121a, 121b may be coupled together by a bridge component 125, at least a portion of which is elevated above the intercondylar passage between medial and lateral base portions 121a, 121b.

During a cruciate-retaining TKA procedure, the surgeon resects portions of tibia 101 corresponding to the footprint of base portion 121, leaving the area associated with the intercondylar passage—which includes tibial eminence 101a that connects to the cruciate ligaments)—intact. Accordingly, base portion 121 is configured to receive tibial eminence 101a in the intercondylar passage interposed between medial and lateral base portions 121a, 121b. In addition, bridge 125 is positioned above the intercondylar passage and is configured to accommodate at least a portion of unresected tibial eminence 101a thereunder.

As will be explained below, certain features of tibial base portion 121 are configured to limit the amount of bone resection that is required to implant tibial insert system 120, without unduly compromising the strength of base portion 121. For example, by providing an elevated bridge 125 as the primary coupling mechanism between medial and lateral base portions 121a, 121b, the amount of bone resection that would otherwise be required to install conventional surface-level or subsurface coupling elements may be reduced or eliminated. Alternatively or additionally, certain embodiments consistent with the present disclosure call for increasing the width of the intercondylar passage from the anterior to the posterior of base portion 121, as shown in FIG. 3. This increase in width further decreases the amount of bone resection, which, in turn, aids in maintaining the attachment strength of tibial eminence 101a.

FIGS. 4A and 4B provide perspective side and top views, respectively, of base portion 121 in accordance with an exemplary embodiment of the present disclosure. As illustrated in FIG. 4A, base portion 121 may include medial and lateral base portions 121a, 121b separated by intercondylar passage 138. Bridge 125 may couple medial and lateral base portions 121a, 121b. Bridge 125 may be elevated above intercondylar passage 138 to allow passage of at least a portion of unresected tibial eminence 101a thereunder.

Medial and lateral base portions 121a, 121b may each include a tray or other type of recession 127 that is configured to receive a corresponding insert portion 123. Medial and lateral base portions 121a, 121b may also include respective lips 126a, 126b, which are formed along the inner (or mesial) edge of the respective base portion. According to one embodiment, lips 126a, 126b increase in height from the posterior to the anterior of base portion 121. As shown in FIG. 4A, lips 126a, 126b have a maximum height toward the anterior of base portion 121, corresponding to the location of bridge 125.

Lips 126a, 126b provide structural support for bridge 125 and are generally designed as having a height sufficient to ensure that the area beneath bridge 125 can accommodate a portion of unresected tibial eminence 101a thereunder. Additionally, lips 126a, 126b may be configured with a maximum height to ensure that bridge 125 does not interfere with proper articulation of femoral component 130. According to one exemplary embodiment, the height of lips 126a, 126b is between about 2 mm and 7 mm.

In addition to providing structural support for bridge 125, lips 126a, 126b may also be configured to act as a guide for femoral component 130, limiting or preventing the possibility of lateral impingement of femoral component 130 with intercondylar passage 138. For example, in certain embodiments, such as that illustrated in FIG. 4B, a mesial edge of medial base portion 121a and a mesial edge of the lateral base portion 121b are substantially non-parallel to one another along a majority of an anterior-posterior length of base portion 121. In particular, the width of the passage between the medial base portion and the lateral base portion increases from the anterior of base portion 121 to the posterior of base portion 121. Although such embodiments allow for increased preservation of the bone that surrounds tibial eminence 101a, they also increase the likelihood of femoral component 130 impinging upon intercondylar passage 138. As such, lips 126a, 126b of base portion 121 may be configured to limit the lateral movement of femoral condyle 130 toward intercondylar passage 138, particularly in situations where the width of the base portion increases toward the posterior of base portion.

Bridge 125 may be coupled between the medial and lateral lips 126a, 126b and may embody the primary strength element for securing medial and lateral base portions 121a, 121b together and preventing the relative movement therebetween. According to one embodiment, and as illustrated in FIG. 4A, bridge 125 may embody an arched structure. As such, bridge 125 may gradually increase in height toward the center of intercondylar passage 138. This increase in height increases the area of the passageway beneath bridge 125. Furthermore, an arched bridge 125 may also be advantageous for distributing compressive forces away from the center of the arch toward the medial and lateral base portions 121a, 121b, where the compressive forces can be more evenly distributed across base portion 121.

According to the embodiment illustrated in FIGS. 4A and 4B, base portion 121 may be configured with openings at both the anterior and posterior edges of bridge 125. These openings may provide a complete passage beneath bridge 125 that can accommodate tibial eminence 101a along the entire anterior-posterior length of base portion 121. By providing a complete passageway between medial and lateral base portions 121 along the entire length of the tibia, a surgeon need only resect portions of the bone to make room for medial and lateral base portions 121a, 121b, leaving most of the tissue associated with tibial eminence 101a intact. By preserving much of the tissue surrounding tibial eminence 101a, much of the natural attachment strength of tibial eminence 101a may be preserved.

FIG. 4B illustrates a configuration of base portion 121 that, alone or in combination with one or more other disclosed embodiments, allows for increased bone preservation at or near tibial eminence 101a. As illustrated in FIG. 4B, medial and lateral base portions 121a, 121b may be arranged such that the width of intercondylar passage 138 increases from the anterior of base portion 121 to the posterior of base portion 121. The precise arrangement of medial and lateral base portions 121a, 121b may be defined by an angle, θ. According to one exemplary embodiment, θ is selected as a value between 7° and 13°. It is contemplated, however, that although many embodiments of tibial implant system 120 are illustrated and described as having an intercondylar passage formed by non-parallel medial and lateral base portions 121a, 121b, certain embodiments may allow for an intercondylar passage formed by substantially parallel medial and lateral base portions 121a, 121b without departing from the scope of the present disclosure.

Figure 5B:
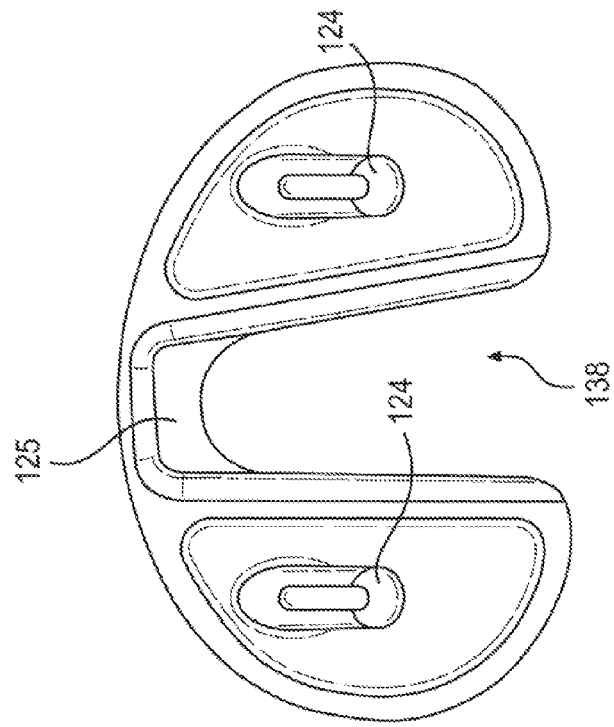
FIG. 5B provides a bottom view of an exemplary cruciate-retaining tibial prosthesis, consistent with the certain disclosed embodiments.
Figure 5A:
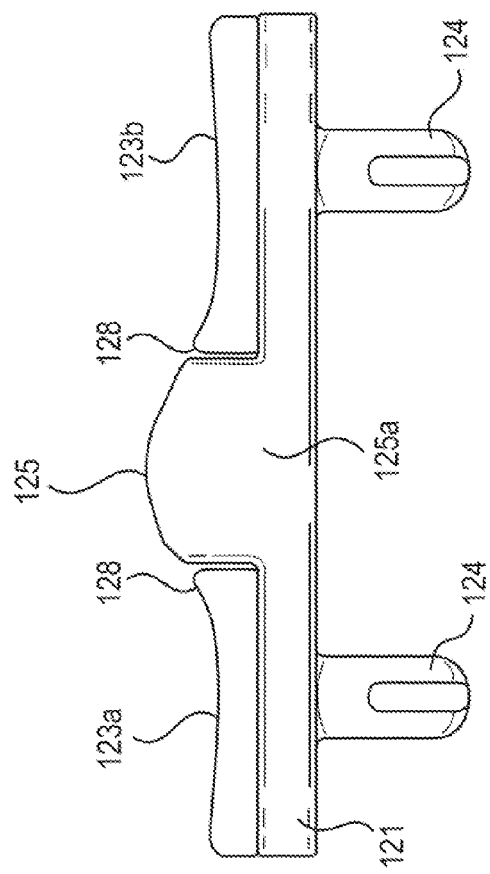
FIG. 5A provides a front view of an exemplary cruciate-retaining tibial prosthesis, consistent with the disclosed embodiments.

FIGS. 5A and 5B illustrate front and bottom views of another embodiment of tibial implant system 120. According to the embodiment illustrated in FIGS. 5A and 5B, bridge 125 may be configured as a partial dome-shaped structure with an opening at the posterior edge of bridge 125. Bridge 125 may also comprise an anterior face portion that extends in the anterior direction and curves downward toward the bottom of base portion 121, forming an anterior face 125a of base portion 121. This anterior face 125a may further increase the strength of bridge 125 by providing an additional surface over which the compressive forces applied to bridge 125 can be distributed.

As illustrated in FIG. 5A, bridge 125 may be asymmetric across intercondylar passage 138 and may be configured to conform to a corresponding asymmetrical shape associated with femoral component 130. More specifically, bridge 125 may be asymmetric about a sagittal plane associated with the base portion 121. Such an asymmetric shape of bridge 125 may limit or prevent abrasive metal-to-metal contact between femoral component 130 and bridge 125.

In contrast with the disclosed embodiments that provide a passage beneath bridge 125, anterior face 125a of base portion 121 of FIGS. 5A and 5B does not permit passage of the tibial eminence 101a along the entire anterior-posterior length of base portion 121. Rather, a small portion of the tibial eminence 101a at the anterior edge of tibia 101 must be resected to accommodate anterior face 125a of base portion 121. Importantly, however, the cavity defined by bridge 125, anterior face 125a, and medial and lateral lips 126a, 126b is configured to receive at least a portion of tibial eminence 101a therewithin, allowing for preservation of a significant majority of tibial eminence 101a and the surrounding bone.

FIG. 5A also illustrates exemplary configurations of insert portions 123 consistent with the disclosed embodiments. Insert portions 123 may comprise a medial insert portion 123a and a lateral insert portion 123b. Medial and lateral insert portions 123a, 123b may be configured to engage a corresponding recess 127 formed in the respective medial and lateral base portions 121a, 121b. Medial and lateral insert portions 123a, 123b may each comprise a flange 128 formed along mesial edge of the respective insert portion. Flanges 128 may be configured to protect at least a portion of the corresponding lip 126a, 126b from contact by femoral component 130.

FIGS. 6A, 6B and 7A, 7B illustrate pairs of corresponding front and cross-section views of exemplary configurations of base portion 121, consistent with certain disclosed embodiments. Specifically, FIGS. 6B and 7A provide cross sectional views (bisected along a sagittal plane associated with the base portion 121 as shown in respective FIGS. 6A and 7A) and show the cross-sectional features of alternate embodiments of bridge 125.

FIGS. 6B and 7B illustrate how the height of bridge 125 varies in a superior direction across the passage, according to certain disclosed embodiments. As shown in FIGS. 6B and 7B, the height of bridge 125 gradually increases across the width of the intercondylar passage. Such an increase in height may provide a greater area beneath bridge 125, which may allow for greater preservation of the surface of tibial eminence 101a.

According to one embodiment, FIG. 6B illustrates a cross-sectional view of bridge 125 having an arched cross-sectional shape. As explained above, the arched cross-sectional shape of bridge 125 distributes compressive forces imposed upon bridge 125 away from the center of the arch toward the medial and lateral base portions 121a, 121b, thereby distributing the compressive forces that are applied to bridge 125 more evenly across base portion 121. According to one embodiment, arched bridge 125 may be substantially dome-shaped or semi-dome shaped; that is, bridge 125 may be partially spherical in shape over at least a portion of the surface of bridge 125. It is important to note that, although FIG. 6 is illustrated as having a substantially dome-shaped structure that is curved in a number of different directions, bridge 125 shown in FIG. 6 need not necessarily be curved in all directions.

For example, as shown in FIG. 7B, one or more surfaces of bridge 125 may comprise a surface that is substantially defined by one or more linear angles. As shown in FIG. 7B, while bridge 125 may be curved in one direction (e.g., across intercondylar passage 138), it may comprise an angled surface, at least a portion of which extends at a superior-posterior angle away from a superior surface of the tibial prosthetic.

As explained, at full extension, the femur is rotated internally relative to the tibia. In other words, as the knee joint travels from flexion to full extension, the front of the femur rotates internally (toward the center of the body) relative to the tibia. Stated another way, the tibia is externally rotated relative to the femur. The amount of femur internal rotation varies among patients, but, for most patients the range is between 0-10° of femur internal rotation, and is typically between 5-8°, and, in some patients is about 7.5°.

FIG. 8A illustrates an exemplary prosthetic component 130. As shown in FIG. 8A, when the femoral and tibial components are aligned with the anterior/posterior ("AP") and medial/lateral ("ML") axes of their respective bones, the femoral component should be internally rotated with respect to the tibial component at an angle $\theta_{TF}$ that lies within the range of about 0-10°, with a preferred range of between 5-8°. According to an exemplary embodiment, the femoral component should be internally offset with a $\theta_{TF}$ of about 7.5°.

Figure 9A:
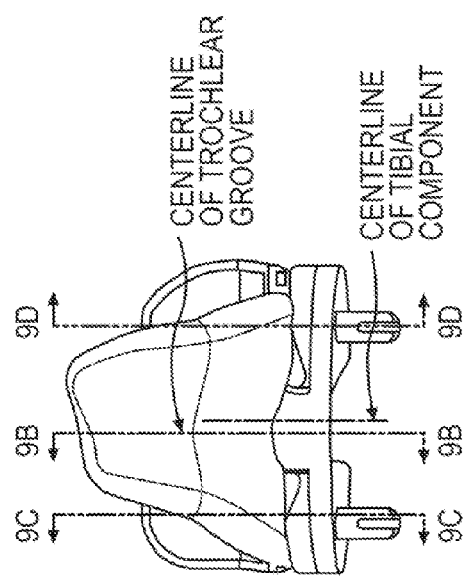
FIGS. 9A-9D provide a front view and side cross-sectional views, respectively, of an exemplary cruciate-retaining prosthetic system having an arcuate bridge, consistent with the disclosed embodiments.

As illustrated in FIG. 9A, internal rotation of the femoral component 130 shifts the femoral component trochlear groove centerline so that it is located on the medial side of the centerline of prosthetic component 130 (denoted by section 9B of FIG. 9A). According to one embodiment, the range of the expected medial offset is between 0 and 6 mm, with the preferred range being about 2 mm to about 4 mm. According to an exemplary embodiment, the medial shift is between about 2.5 mm and 3.5 mm.

To ensure that the tibial component bridge does not impinge with the femoral component at full extension, the bridge of the tibial component can be offset medially from the tibial component centerline, as shown in the exemplary embodiments illustrated in FIGS. 8B, 9A, and 12B-12D. The expected offset range is 0-6 mm, the preferred range is 2-4 mm, and the preferred embodiment range is 2.5-3.5 mm.

To prevent bridge impingement with the femoral component, the height of the top of bridge 125 (as shown, for example, in FIG. 10B) is limited to the range of about 10-20 mm, with a preferred range of 12-18 mm. According to an exemplary embodiment, the height range of tibial bridge 125 is between about 13 min and about 17 mm.

Figure 10A:
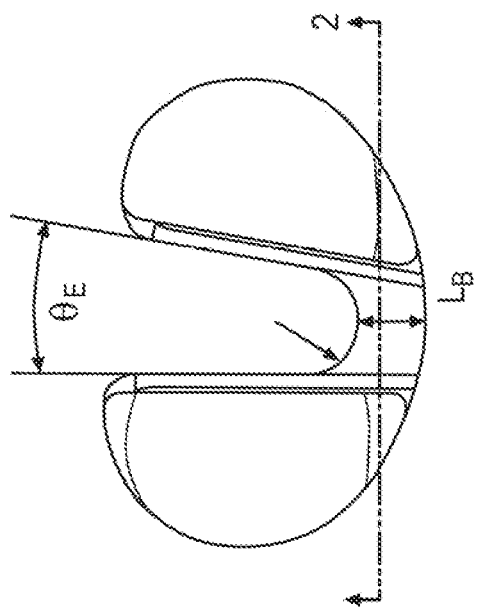
FIGS. 10A and 10B provide a top view and front cross-sectional view, respectively, of an exemplary tibial component having an arcuate bridge, consistent with the disclosed embodiments.
Figure 10B:
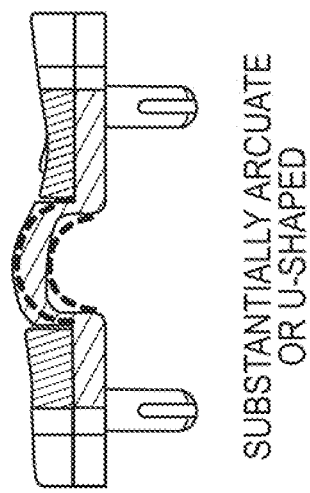

To also reduce the risk of impingement, the outer shape of the bridge can substantially match the coronal shape of the femoral component trochlear groove, which is substantially arcuate, L-shaped, or convex. Such embodiments are illustrated in the cross-section views shown, for example, in FIGS. 8B and 10B. According to an exemplary embodiment, the coronal radius of the outer bridge shape shown in FIG. 10B is between 10-26 mm, with a preferred range of between about 12 mm and about 24 mm. According to an exemplary embodiment, the range of the radius used to define the coronal shape of tibial prosthetic of FIG. 10B is between about 14 mm and about 18 mm.

Figure 9B:
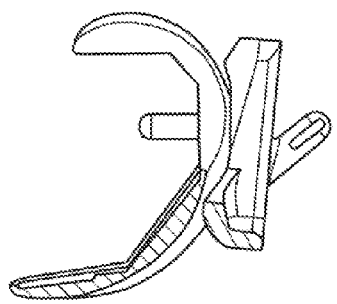
Figure 9C:
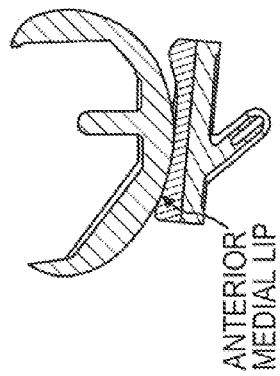
Figure 9D:
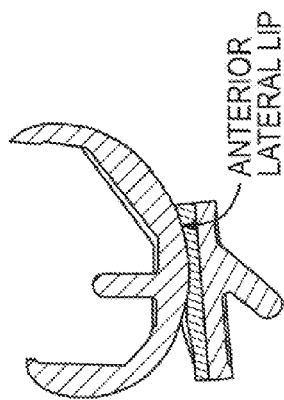

The tibial articular surfaces can also be configured to ensure that the femoral component does not impinge on the tibial component bridge. For example, FIGS. 9C and 9D illustrate interior regions of the medial and lateral tibial inserts that have sagittal arcuate lips that substantially match the femoral component, which limits anterior translation of the femoral component (as shown in FIG. 9B), thus preventing impingement. According to one embodiment, the range of the sagittal radii that define the curvature of the arcuate lips of the tibial inserts is between 25-80 mm, with a preferred range of between about 35 and about 70 mm. According to an exemplary embodiment, the range is between about 45 mm and about 60 mm. Further, the height of the sagittal lips measured from the highest point of the lip to the lowest point in the articular surface may have an expected range of between about 1-15 mm, with a preferred range of between about 2 mm and about 12 mm. According to an exemplary embodiment, the height of the highest point of the sagittal arcuate lips is between about 3 mm and about 9 mm.

Furthermore, as illustrated in FIG. 8B, the mesial edges of the tibial inserts near the tibial eminence can have coronal arcuate radii that substantially match the femoral component, which limits mediolateral translation of the femoral component, further assisting in the limiting impingement. According to an exemplary embodiment, the range of the coronal radii that defines the shape of the tibial insert 123 in the medial/lateral direction is between about 20 mm and 52 mm, with the preferred embodiment ranging from about 24 mm and about 48 mm. According to an exemplary embodiment, the radial range for defining the curvature of tibial inserts 123 in the medial/lateral direction is between about 30 mm and about 36 mm. The height of the coronal lips measured from the highest point of the lip to the lowest point in the articular surface has an exemplary range of 1-8 mm, with a preferred range of between about 2 mm and about 7 mm. According to an exemplary embodiment, the height range of the articular surface is between about 3 mm and about 6 mm.

As explained, to spare the ACL, the tibial bridge should not impinge on the ACL, and should also retain sufficient tibial eminence bone. Removing bone from the anterior tibial eminence weakens the boney structure and potentially creates stress risers. During demanding activities when the ACL is exposed to tension, a compromised anterior tibial eminence can result in ACL avulsion. Therefore, the shape of the tibial component bridge is critically important, as it determines how much anterior tibial eminence bone is removed. Additionally, the bridge should be strong enough to withstand the expected loads imparted during activities of daily living.

As with the femoral component 130, the bridge can be centered or shifted in the medial direction from the centerline of tibial base component 120, as illustrated in FIGS. 8B and 10B. According to one embodiment, the medial offset ranges from between about 0 mm to about 6 mm, with a preferred range between about 2 mm and about 4 mm. According to an exemplary embodiment, the medial offset is between 2.5 mm and 3.5 mm. As shown in FIG. 10A, the tibial bridge can be shaped around the ACL insertion footprint in an arcuate or U-shaped form. According to one embodiment, the radius range that defines the curvature of the arcuate shape is 4.25-13.5 mm, with the preferred range between about 5.25 mm and about 12.5 mm. According to an exemplary embodiment, the radial range that defines the curvature is between about 6.25 mm and about 11.5 mm.

As also shown in the FIG. 10A, the anterior/posterior (AP) length of the bridge $L_B$ should be selected to prevent impingement with the ACL. According to one embodiment, the AP length is between about 4 mm and about 15 mm, with the preferred range between about 7-13 mm. According to an exemplary embodiment, length $L_B$ of tibial bridge 125 between about 8 mm and about 12 mm. As explained above, to preserve more bone toward the posterior of the tibia and to aid in lateral compartment access adjacent to the patellar ligament, the lateral mesial edge can be angled away from the medial mesial edge toward the posterior of tibial implant system 120, as shown in FIG. 10A. According to one embodiment, the angle $\theta_E$ formed by the offset is about 1-20°, with a preferred range between about 7° and 13°. According to an exemplary embodiment, $\theta_E$ is about 10°.

The medial tibia bone compartment is substantially concave in the sagittal plane and consequently has a raised anterior lip. The lateral tibia compartment is substantially flat or convex in the sagittal plane, and therefore has a little to no anterior lip. In the coronal view, this shape difference between the medial and lateral compartments results in the anterior medial eminence being taller than the anterior lateral eminence. To spare as much bone as possible, tibial component 120 may be configured so that the height toward the medial bridge is greater than the height toward the lateral side bridge. According to one embodiment, the height range toward the medial side is 8-15 mm, with the preferred range being between about 9 mm and 14 mm. According to one exemplary embodiment, and the height range of tibial bridge 125 toward the medial side is between about 10 mm and about 13 mm. Furthermore, the height toward the lateral side of tibial bridge range is 6-13 mm, with a preferred range between 7-12 mm. According to an exemplary embodiment, the height toward the lateral side of tibial bridge is between about 8 mm and about 11 mm.

As shown in the coronal view cross-section of tibial bridge 125 illustrated in FIG. 10B, the inner tibia facing side of the bridge may be substantially arcuate, L-shaped, or concave. According to one embodiment, the arcuate radius range is between about 4.25-13.5 mm, with a preferred range between about 5.25-12.5 mm. According to an exemplary embodiment, the arcuate radius range is between 6.25 mm and 11.5 mm. The width of the inner tibia facing side has a range of between about 4.25 mm and about 13.5 mm, with a preferred range of about 5.25-12.5 mm. According to an exemplary embodiment the width of the underside of tibial bridge 125 ranges between about 6.25 mm and about 11.5 mm.

The maximum height of the inner tibia facing side of tibial bridge 125 is between about 5-15 mm, with a preferred range between about 7 mm and about 13 mm. According to an exemplary embodiment the maximum height ranges between about 8 mm and 12 mm. Since the anterior medial eminence is taller than the lateral eminence, the medial height range is 3-10 mm, with a preferred range of about 4-9 mm. According to an exemplary embodiment, the medial height range is between 5 mm and 8 mm. The lateral height range is between about 1 mm and about 8 mm, with a preferred range between about 2 mm and 7 mm. According to an exemplary embodiment, the lateral height range between about 3 mm and about 6 mm.

To aid in the strength of tibial bridge 125, the coronal cross-sectional thickness can be constant, variable, or non-uniform, as shown, for example, in FIGS. 10B and 12A-12D. The range of thickness of tibial bridge 125 is 1-10 mm, with a preferred range between about 3 mm and 7 mm. According to an exemplary embodiment, the thickness of tibial bridge 125 ranges between about 4 mm and about 6 mm.

To reduce stress risers, the corner of the eminence where the horizontal resection meets the vertical wall resection can be filleted. The tibial component 120 can have a complimentary filleted shape (FIGS. 10B and 12A-12D), or it can be chamfered to accommodate the filleted corner of the tibial eminence. According to one embodiment, the range for this fillet radius is 1-8 mm, with a preferred range between about 2 mm and about 6 mm. According to an exemplary embodiment the range for the fillet radius is between about 3 mm and about 5 mm.

Similarly, to aid in tibial component strength, the region where the tibial plate meets the bridge can be blended, tapered, or chamfered to help distribute the stress (FIG. 10B). The expected range for this fillet radius is between 1-8 mm, with a preferred range between 2 mm and 6 mm. According to an exemplary embodiment, the fillet radius is between about 3 mm and about 4 mm.

Figure 11A:
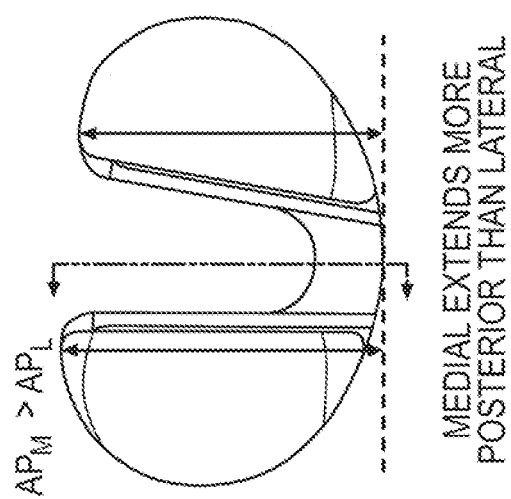
FIGS. 11A and 11B provide a top view and side cross-sectional view, respectively, of an exemplary tibial component having an arcuate bridge, consistent with the disclosed embodiments.

The resected bone in a transverse view has a longer medial AP length than the lateral AP length. The medial compartment extends more posterior than the lateral compartment. For better bone coverage, the tibial component can have a longer medial AP length and extend more posterior than the lateral AP length (FIG. 11A). The expected range for this AP length difference (additional posterior medial AP length extension) is 1-6 mm, with a preferred range between about 2 mm and about 5 mm. According to an exemplary embodiment, the range of length difference is between about 3 mm and about 4 mm.

Figure 11B:
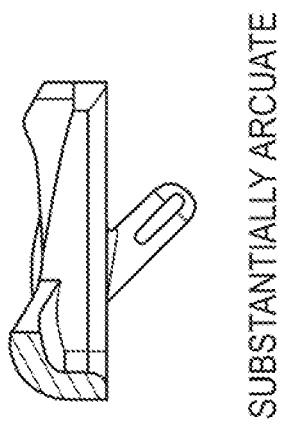
Figure 12A:
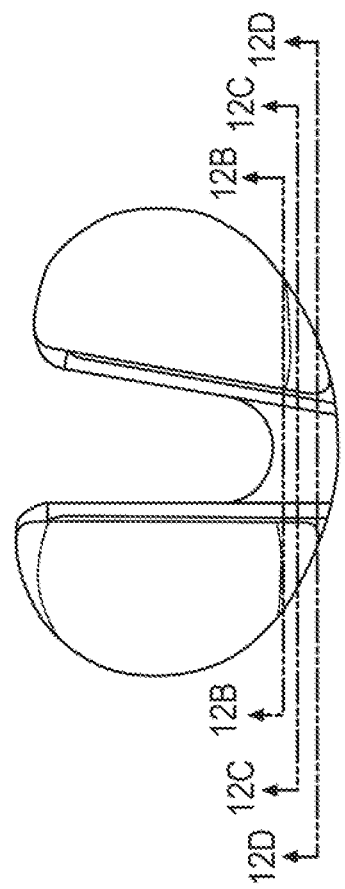
FIGS. 12A-12D provide a top view and front cross-sectional views, respectively, of an exemplary tibial component having an arcuate bridge, consistent with the disclosed embodiments.
Figure 12B:
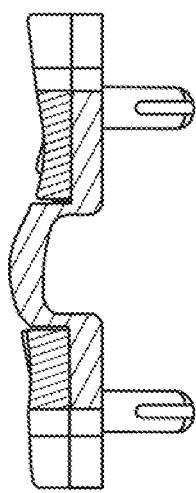
Figure 12C:
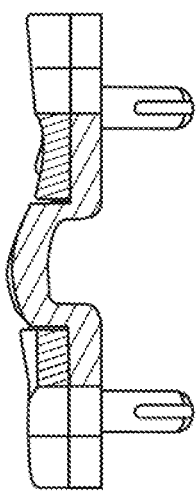
Figure 12D:
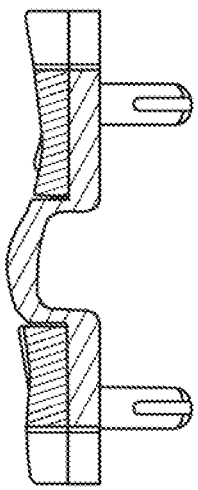
Figure 13C:
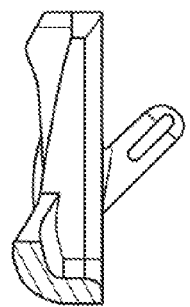
FIGS. 13A-13D provide a top view and side cross-sectional views, respectively, of an exemplary tibial component having an arcuate bridge, consistent with the disclosed embodiments.
Figure 13D:
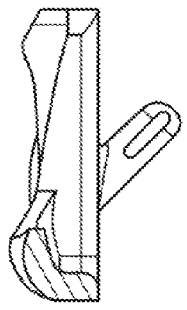
Figure 13A:
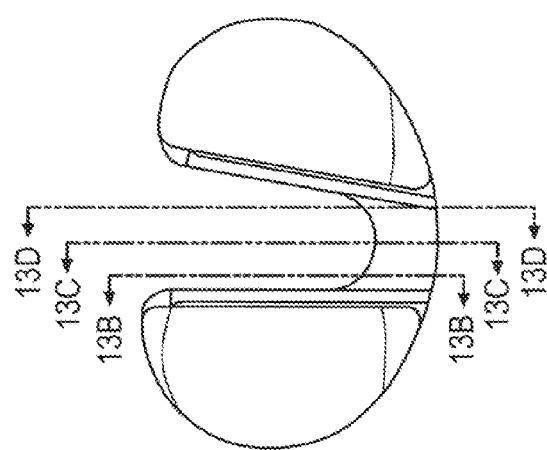
Figure 13B:
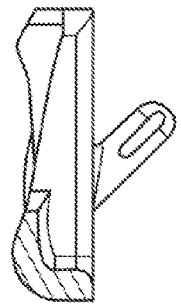

In the sagittal view cross-section of the bridge (FIG. 11B), the inner tibia facing side of the bridge is substantially arcuate, L-shaped, or concave. The expected arcuate radius range is 3-20 mm, the preferred range is 4-15 mm, and the preferred embodiment range is 5-10 mm. To aid in bridge strength, the sagittal cross-sectional thickness can be constant, variable, or non-uniform (FIGS. 11B and 13A-13B). The expected thickness range is 1-10 mm, the preferred range is 3-7 mm, and the preferred embodiment range is 4-6 mm. To help distribute the stress from the bridge and to keep cement from extruding into the tibial component compartments, the mesial tibial component implant wall can be tapered or have a constant height (FIG. 11B). The expected wall height from the bottom of the tibial component is 8-15 mm, the preferred range is 10-14 mm, and the preferred embodiment is 12 mm. The expected wall taper angle from horizontal is 1-20°, the preferred range is 5-15°, and the preferred embodiment range is 8-12°.

Figure 16B:
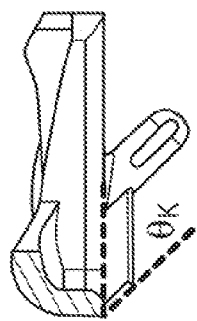
FIGS. 16A and 16B provide a top view and side cross-sectional view, respectively, of an exemplary tibial component having an arcuate bridge and an angled, arcuate underside keel, consistent with the disclosed embodiments.
Figure 17C:
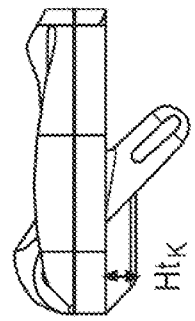
FIGS. 17A-17C provide a front view, bottom view, and side cross-sectional view, respectively, of an exemplary tibial component having an arcuate bridge and an angled, arcuate underside keel, consistent with the disclosed embodiments.
Figure 16A:
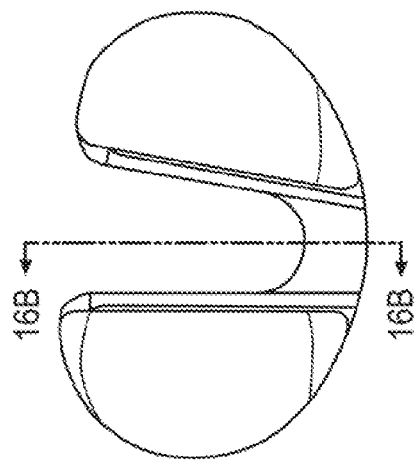
Figure 17A:
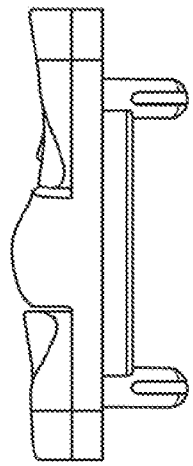
Figure 17B:
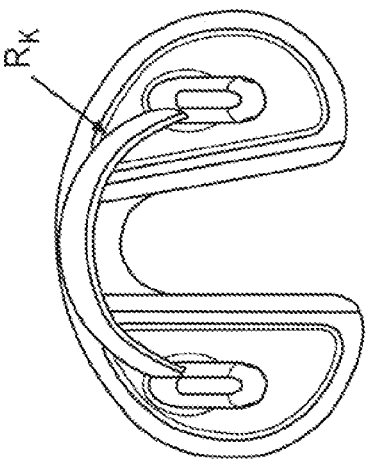
Figure 18A:
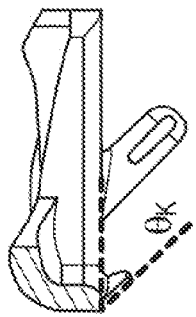
FIGS. 18A and 18B provide a top view and side cross-sectional view, respectively, of an exemplary tibial component having an arcuate bridge and an angled underside keel, consistent with the disclosed embodiments.
Figure 18B:
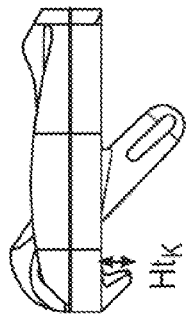
Figure 19C:
FIGS. 19A-19C provide a front view, bottom view, and side cross-sectional view, respectively, of an exemplary tibial component having an arcuate bridge and an angled underside keel, consistent with the disclosed embodiments.
Figure 19A:
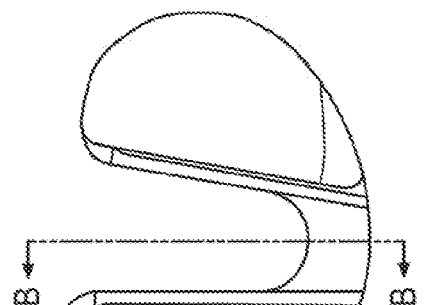
Figure 19B:
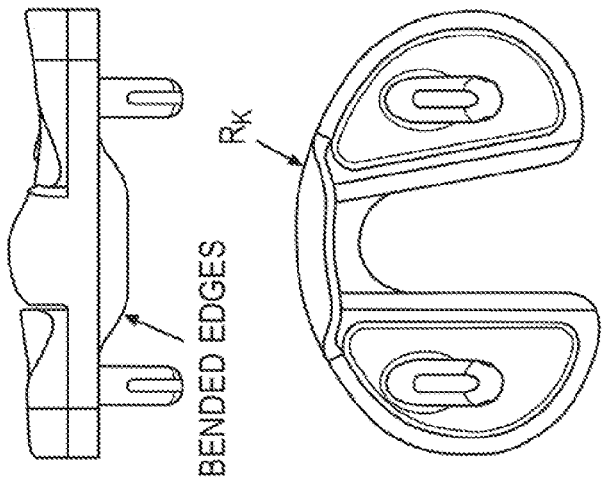

To aid in strength and to distribute stress from the bridge, a keel can be included. The keel is substantially straight in cross-section because it is prepared with a cutting burr or impaction-type punch, and the preparation direction of these tools are straight. The keel can be perpendicular to the baseplate (FIGS. 14A, 14B, and 15A-15C) or it can be angled posteriorly to help eliminate interference with the femur during keel preparation (FIGS. 16A, 16B). The expected posterior angle from horizontal is 30-90°, the preferred range is 40-70°, and the preferred embodiment range is 45-75°. In a transverse view the keel can have a substantially linear footprint or a substantially arcuate footprint (FIG. 15B). The expected footprint radius 10-200 mm, the preferred range is 15-60 mm, and the preferred embodiment range is 20-50 mm. The keel can be tangent to the front edge of the tibial component footprint (FIGS. 14B, 15B, 16B, and 17B), or it can be offset posteriorly to prevent removal of anterior cortical tibia bone. The expected posterior offset is 0.5-10 mm, the preferred range is 1-8 mm, and the preferred embodiment range is 2-6 mm. The height of the keel is proportional to the strength, but a taller keel will also weaken the ACL attachment site because it begins to undercut the ACL insertion site (FIG. 16B). Therefore, it is desirable to minimize keel height or eliminate it entirely. The expected keel height is 1-15 mm, the preferred range is 2-10 mm, and the preferred embodiment range is 3-6 mm. The keel can also be a constant height or it can taper away from the bridge medial-lateral and anterior-posterior (FIG. 19A).

The systems and features associated with tibial insert system 120 described herein provide a solution for decreasing the amount of bone resection that may be required in the area surrounding tibial eminence 101a, without compromising the strength of the prosthetic. Specifically, by providing an elevated bridge that is configured to traverse the intercondylar passage between the medial and lateral sections of base portion 121, tibial implant system 120 limits the amount of bone resection associated with tibial eminence 101a. Bone resection can be further reduced by increasing the width of the intercondylar passage between the medial and lateral sections of base portion 121a, 121b from the anterior to the posterior of tibial implant system 120. The strength of tibial implant system 120 may be maintained by configuring the bridge as an arched, angled, and/or dome-shaped structure that transfers the compressive forces applied to the bridge away from the center of the bridge toward the medial and lateral sections of base portion 121a, 121b, which have greater surface area over which to distribute such forces. It will be apparent to those skilled in the art that various modifications and variations can be made to the disclosed femoral implants and associated methods for designing the same. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A tibial prosthesis comprising:
   a medial base portion configured to engage a medial surface of a tibia;

a lateral base portion configured to engage a lateral surface of the tibia, wherein at least a portion of the medial and lateral base portions are separated by a passage interposed therebetween; and a bridge coupling the medial base portion and the lateral base portion, wherein at least a portion of the bridge is elevated above a portion of the passage between the medial base portion and the lateral base portion, the bridge defining an underlying area that receives at least a portion of a tibial eminence when the tibial prosthesis is engaged with the tibia, wherein a height of the bridge varies in a superior direction across the passage; and wherein the medial base portion and the lateral base portion each comprise a lip formed along a respective mesial edge, wherein the lip increases in height from a posterior portion of the tibial prosthesis to an anterior portion of the tibial prosthesis, the bridge comprising a posterior edge defining a posterior opening, wherein the lips extend to the posterior edge and form, at least in part, the posterior opening, the lips providing support to allow the bridge to accommodate the at least a portion of the tibial eminence.

2. The tibial prosthesis of claim 1, wherein the bridge is substantially curved in the superior direction across the passage.

3. The tibial prosthesis of claim 2, wherein the bridge comprises an arch.

4. The tibial prosthesis of claim 3, wherein the bridge is substantially dome-shaped.

5. The tibial prosthesis of claim 1, wherein at least a section of the bridge comprises a linear angle that extends at a superior-posterior angle away from an inferior surface of the tibial prosthesis.

6. The tibial prosthesis of claim 1, wherein the mesial edge of the medial base portion and the mesial edge of the lateral base portion are substantially parallel to one another along a majority of an anterior-posterior length of the tibial prosthesis.

7. The tibial prosthesis of claim 1, wherein the mesial edge of the medial base portion and the mesial edge of the lateral base portion are substantially non-parallel to one another along a majority of an anterior-posterior length of the tibial prosthesis.

8. The tibial prosthesis of claim 7, wherein a width of the passage between the medial base portion and the lateral base portion increases from the anterior portion of the tibial prosthesis to the posterior portion of the tibial prosthesis.

9. The tibial prosthesis of claim 1, wherein the passage extends along an entirety of a length between medial and lateral base portions.

10. The tibial prosthesis of claim 1, wherein the bridge comprises an anterior face portion of the tibial prosthesis such that, when the tibial prosthesis is engaged with the tibia, the bridge and mesial edges of the medial and lateral base portions define a cavity for receiving a portion of the tibial eminence.

11. The tibial prosthesis of claim 1, further comprising medial and lateral insert portions, each of which is configured to engage a corresponding recess formed in the respective base portion and comprises a flange formed along a mesial edge of the respective insert portion, wherein the flange is configured to protect at least a portion of the lip from contact by a femoral component.

12. The tibial prosthesis of claim 1, wherein the tibial prosthesis has a centerline and the bridge is offset medially a distance from the centerline.

13. The tibial prosthesis of claim 1, wherein a maximum height of each of the lips is adjacent the bridge.

14. The tibial prosthesis of claim 1, wherein the bridge at least partially defines an anterior opening such that a complete passage is formed through the bridge from the posterior opening to the anterior opening.

15. The tibial prosthesis of claim 1, wherein the bridge comprises an anterior face closing the bridge at an anterior section thereof, the anterior face extending downwards a predetermined distance so that the anterior face is not configured to preserve at least a portion of the tibial eminence.

16. The tibial prosthesis of claim 1, wherein the bridge is asymmetric about a sagittal plane associated with the tibial prosthesis.

17. The tibial prosthesis of claim 1, wherein an apex of the posterior edge of the bridge defines a maximum height of the bridge.

18. The tibial prosthesis of claim 17, wherein a maximum height of each of the lips is adjacent the bridge.

19. A tibial prosthesis comprising:
a medial base portion configured to engage a medial surface of a tibia and comprising a lip formed along a mesial edge of the medial base portion;
a medial insert portion configured to engage a recess formed in the medial base portion, the medial insert portion comprising a flange formed along a mesial edge of the medial insert portion in a direction substantially aligned with the mesial edge of the medial insert portion, such that when the medial insert portion engages the recess formed in the medial base portion, the flange is positioned adjacent to a distal surface of the lip and configured to protect at least a portion of the lip from contact by a femoral component;
a lateral base portion configured to engage a lateral surface of the tibia and comprising a lip formed along a mesial edge of the lateral base portion;
a lateral insert portion configured to engage a recess formed in the lateral base portion, the lateral insert portion comprising a flange formed along a mesial edge of the lateral insert portion in a direction substantially aligned with the mesial edge of the lateral insert portion, such that when the lateral insert portion engages the recess formed in the lateral base portion, the flange is positioned adjacent to a distal surface of the lip and configured to protect at least a portion of the lip from contact by a femoral component; and
an arched bridge coupling the medial base portion and the lateral base portion, wherein at least a portion of the arched bridge is elevated above a portion of a passage interposed between the medial base portion and the lateral base portion, the arched bridge defining an underlying area that accommodates at least a portion of a tibial eminence when the tibial prosthesis is engaged with the tibia, wherein a width of the passage between the medial base portion and the lateral base portion increases from an anterior portion of the tibial prosthesis to a posterior portion of the tibial prosthesis.

20. The tibial prosthesis of claim 19, wherein the arched bridge is substantially dome-shaped.

21. The tibial prosthesis of claim 19, wherein the passage extends along an entirety of a length between medial and lateral base portions.

22. The tibial prosthesis of claim 19, wherein the arched bridge comprises an anterior face portion of the tibial prosthesis such that, when the tibial prosthesis is engaged with the tibia, the arched bridge and mesial edges of the medial and lateral base portions define a cavity for receiving a portion of the tibial eminence.

23. The tibial prosthesis of claim 19, wherein the bridge comprises a posterior edge defining a posterior opening, the lips extending to the posterior edge and forming, at least in part, the posterior opening.

24. The tibial prosthesis of claim 19, wherein the bridge at least partially defines an anterior opening such that a complete passage is formed through the bridge from the posterior opening to the anterior opening.

25. The tibial prosthesis of claim 19, wherein the bridge comprises an anterior face closing the bridge at an anterior section thereof, the anterior face extending downwards a predetermined distance so that the anterior face is not configured to preserve at least a portion of the tibial eminence.

* * * * *